US012601618B2

(12) United States Patent
Fukushima et al.

(10) Patent No.: US 12,601,618 B2
(45) Date of Patent: Apr. 14, 2026

(54) CASING FOR LIVESTOCK SENSOR AND LIVESTOCK SENSOR

(71) Applicant: DAIKIN INDUSTRIES, LTD., Osaka (JP)

(72) Inventors: Toshiyuki Fukushima, Osaka (JP); Hirofumi Mukae, Osaka (JP); Kenji Ishii, Osaka (JP); Yoshito Tanaka, Osaka (JP); Masaji Komori, Osaka (JP); Takumi Shimosuki, Osaka (JP); Akiyoshi Yamauchi, Osaka (JP); Yosuke Kishikawa, Osaka (JP); Hirokazu Aoyama, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 272 days.

(21) Appl. No.: 18/330,716

(22) Filed: Jun. 7, 2023

(65) Prior Publication Data

US 2023/0357553 A1 Nov. 9, 2023

Related U.S. Application Data

(63) Continuation of application No. PCT/JP2021/044402, filed on Dec. 3, 2021.

(30) Foreign Application Priority Data

Dec. 10, 2020 (JP) ................................ 2020-205071

(51) Int. Cl.
*G01D 11/24* (2006.01)
*A01K 11/00* (2006.01)
(Continued)

(52) U.S. Cl.
CPC .......... *G01D 11/245* (2013.01); *A01K 11/007* (2013.01); *A01K 29/005* (2013.01);
(Continued)

(58) Field of Classification Search
CPC . A61B 5/6871; A61B 5/6861; A61B 2503/40; A61B 2562/162; A01K 11/007;
(Continued)

(56) References Cited

U.S. PATENT DOCUMENTS

2001/0029317 A1 10/2001 Hayakawa
2003/0211264 A1 11/2003 Farnsworth et al.
(Continued)

FOREIGN PATENT DOCUMENTS

AT 505607 A1 2/2009
EP 1 892 649 A2 2/2008
(Continued)

OTHER PUBLICATIONS

MatWeb ("Overview of materials for Polyperfluoroalkoxyethylene"—available online at https://web.archive.org/web/20151001234537/https://www.matweb.com/search/datasheettext.aspx?matguid=bcef91c18341484bba33eef37344bc0d—via the Wayback Machine (Year: 2015).*

(Continued)

*Primary Examiner* — Benjamin R Schmitt
(74) *Attorney, Agent, or Firm* — Sughrue Mion, PLLC

(57) ABSTRACT

A housing for a livestock sensor, the housing including: a resin having a coefficient of kinetic friction of 0.40 or lower and a coefficient of static friction of 0.10 or lower, and the resin being other than polytetrafluoroethylene. Also disclosed is a livestock sensor including the housing and a detector inside the housing.

8 Claims, 1 Drawing Sheet

(51) Int. Cl.

| | |
|---|---|
| ***A01K 29/00*** | (2006.01) |
| ***A61B 5/00*** | (2006.01) |
| ***C08L 23/0892*** | (2025.01) |
| ***C08L 27/12*** | (2006.01) |
| ***C08L 27/18*** | (2006.01) |
| ***C08L 27/20*** | (2006.01) |

(52) U.S. Cl.
CPC ........ *A61B 5/6871* (2013.01); *C08L 23/0892* (2013.01); *C08L 27/12* (2013.01); *C08L 27/18* (2013.01); *C08L 27/20* (2013.01); *A61B 5/6861* (2013.01); *A61B 2503/40* (2013.01); *A61B 2562/162* (2013.01); *Y02A 40/70* (2018.01)

(58) Field of Classification Search
CPC .... A01K 29/005; G01D 11/24; G01D 11/245; Y02A 40/70; C08L 23/0892; C08L 27/12; C08L 27/18; C08L 27/20
See application file for complete search history.

(56) References Cited

U.S. PATENT DOCUMENTS

| | | | |
|---|---|---|---|
| 2004/0133131 A1 | 7/2004 | Kuhn et al. | |
| 2008/0042849 A1 | 2/2008 | Saito et al. | |
| 2012/0088988 A1 | 4/2012 | Sato et al. | |
| 2012/0121908 A1 | 5/2012 | Aruga | |
| 2014/0090490 A1* | 4/2014 | Kopp ..................... | G01D 11/24 73/864.91 |
| 2016/0289399 A1 | 10/2016 | Underwood et al. | |
| 2016/0353710 A1 | 12/2016 | Laporte Uribe | |
| 2017/0111128 A1* | 4/2017 | Hammerschmidt ... | A01K 1/031 |
| 2017/0252016 A1 | 9/2017 | Wrigglesworth et al. | |
| 2017/0333240 A1 | 11/2017 | Stangenes et al. | |
| 2019/0322546 A1 | 10/2019 | Sugiyama et al. | |
| 2023/0309514 A1 | 10/2023 | Mukae et al. | |
| 2023/0312777 A1 | 10/2023 | Ishii et al. | |

FOREIGN PATENT DOCUMENTS

| | | | |
|---|---|---|---|
| EP | 3 155 899 | A1 | 4/2017 |
| JP | 8-272296 | A | 10/1996 |
| JP | 2007185522 | A | 7/2007 |
| JP | 2009-28245 | A | 2/2009 |
| JP | 2009125101 | A | 6/2009 |
| JP | 2011-89828 | A | 5/2011 |
| JP | 2011-104158 | A | 6/2011 |
| JP | 2017-123225 | A | 7/2017 |
| JP | 2018-113902 | A | 7/2018 |
| JP | 2019-516495 | A | 6/2019 |
| JP | 2020-127747 | A | 8/2020 |
| WO | 2010/147175 | A1 | 12/2010 |
| WO | 2011/013576 | A1 | 2/2011 |
| WO | 2022/124221 | A1 | 6/2022 |

OTHER PUBLICATIONS

Teflon.com ("Properties of Teflon™ Industrial Coatings"—available online at https://www.teflon.com/en/products/coatings) (Year: 2019).*

TefCap.com ("Fluoropolymer Resins"—available online at https://tefcap.com/fluoropolymer-fep-pfa-ptfe-peek-halar-kynar-resins/ snapshot taken by the wayback machine in 2019—see PFA section, which establishes the resin is melt-fabricable) (Year: 2019).*

Communication dated Oct. 2, 2024 issued by the European Patent Office in application No. 21903318.0.

Communication dated Oct. 2, 2024 issued by the European Patent Office in application No. 21903313.1.

Extended European Search Report issued Sep. 17, 2024 in European Application No. 21903320.6.

International Search Report for PCT/JP2021/044384 dated Dec. 28, 2021 (PCT/ISA/210).

International Search Report for PCT/JP2021/044397 dated Dec. 28, 2021 (PCT/ISA/210).

International Search Report for PCT/JP2021/044402 dated Dec. 28, 2021 (PCT/ISA/210).

International Search Report for PCT/JP2021/044420 dated Dec. 28, 2021 (PCT/ISA/210).

International Preliminary Report on Patentability dated Jun. 13, 2023 with a Translation of the Written Opinion of the International Searching Authority in Application No. PCT/JP2021/044384.

International Preliminary Report on Patentability dated Jun. 13, 2023 with a Translation of the Written Opinion of the International Searching Authority in Application No. PCT/JP2021/044397.

International Preliminary Report on Patentability dated Jun. 13, 2023 with a Translation of the Written Opinion of the International Searching Authority in Application No. PCT/JP2021/044402.

International Preliminary Report on Patentability dated Jun. 13, 2023 with a Translation of the Written Opinion of the International Searching Authority in Application No. PCT/JP2021/044420.

Coating Technology, vol. 9, Compiled by the Coating Technology Training Class of the Ministry of Raw Materials and Fuel Chemical Industry, Chemical Industry Press, First Edition, Apr. 1983 (6 pages).

Plastics Industry Dictionary, Edited by Su Jiaqi, Chemical Industry Press, First Edition, Dec. 1989 (7 pages).

* cited by examiner

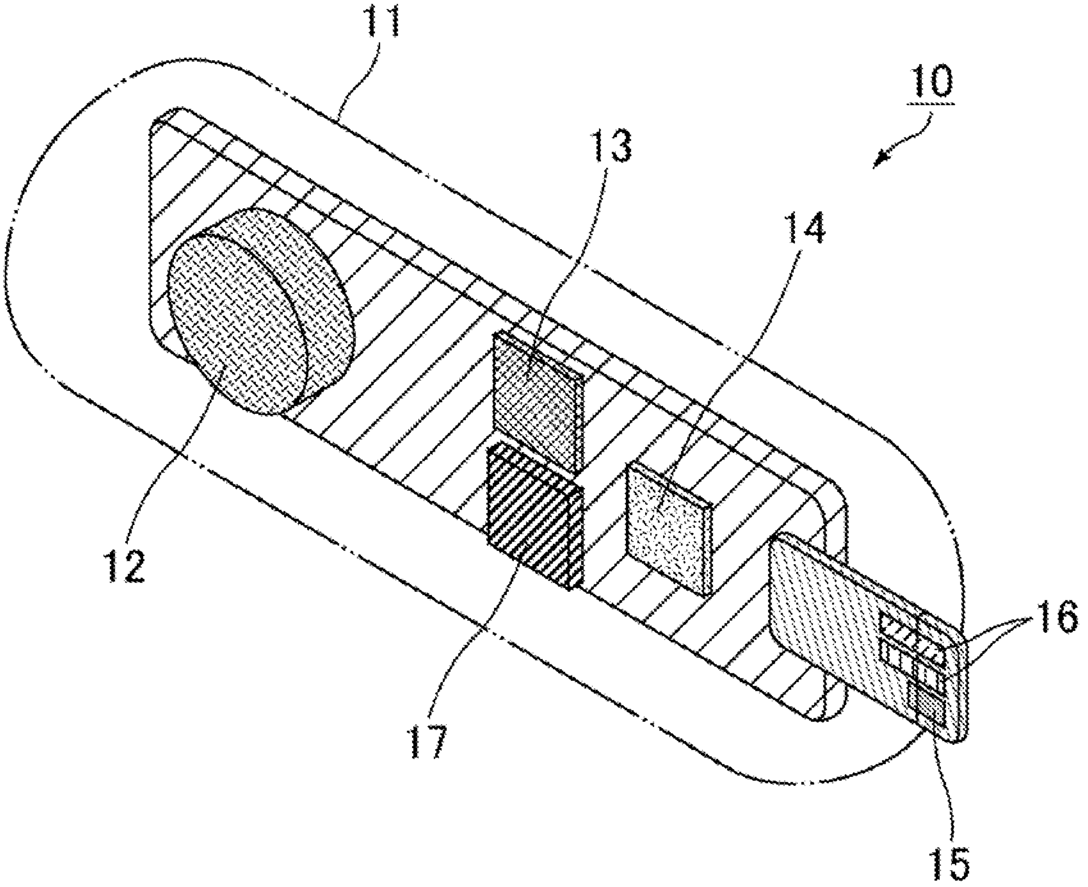
11
10
13
14
12
17
16
15

CASING FOR LIVESTOCK SENSOR AND LIVESTOCK SENSOR

This application is a Rule 53(b) Continuation of International Application No. PCT/JP2021/044402 filed Dec. 3, 2021, claiming priority based on Japanese Patent Application No. 2020-205071 filed Dec. 10, 2020, the respective disclosures of which are incorporated herein by reference in their entireties.

TECHNICAL FIELD

The disclosure relates to housings for livestock sensors and livestock sensors.

BACKGROUND ART

In the recent study in the field of livestock production, it has been considered to place sensors in the cattle's body to manage the health and breeding of cattle.

Patent Literature 1 discloses a detection device that detects the internal state of the cattle rumen, including a stainless-steel container and a resin (e.g., polypropylene) cap in a tapered shape.

CITATION LIST

Patent Literature

Patent Literature 1: WO 2010/147175

SUMMARY

The disclosure relates to a housing for a livestock sensor, the housing including: a resin having a coefficient of kinetic friction of 0.40 or lower and a coefficient of static friction of 0.10 or lower.

Advantageous Effects

The disclosure can provide a housing for a livestock sensor capable of constituting a livestock sensor that can be easily administered orally to livestock, and a livestock sensor including the same.

BRIEF DESCRIPTION OF THE DRAWINGS

The FIGURE is a cross-sectional view of an exemplary structure of a livestock sensor.

DESCRIPTION OF EMBODIMENTS

Housings for livestock sensors have conventionally been designed to have a shape and size that allows easy oral administration.

As a result of intensive studies from a different perspective than before, the present inventors have found that a housing formed from a resin having a specific coefficient of kinetic friction and a specific coefficient of static friction can constitute a livestock sensor that can be easily administered to livestock orally. Thus, the housing for a livestock sensor of the disclosure was completed.

The disclosure will be specifically described below.

The housing for a livestock sensor of the disclosure contains a resin having a coefficient of kinetic friction of 0.40 or lower and a coefficient of static friction of 0.10 or lower. A livestock sensor including a housing formed from a resin having a coefficient of kinetic friction of 0.40 or lower and a coefficient of static friction of 0.10 or lower is slippery and therefore facilitates swallowing of the sensor by livestock, allowing for easy oral administration. Such a livestock sensor enables highly reliable data acquisition without giving stress to livestock. Use of such a resin also reduces the limitation on the shape or size of the housing and therefore can increase the design flexibility.

The coefficient of kinetic friction is preferably 0.10 or lower, more preferably 0.08 or lower, still more preferably 0.04 or lower. The coefficient of kinetic friction may be 0.01 or higher.

The coefficient of static friction is preferably 0.07 or lower, more preferably 0.05 or lower, still more preferably 0.03 or lower. The coefficient of static friction may be 0.01 or higher.

The coefficient of kinetic friction and the coefficient of static friction are each measured in conformity with JIS K 7125 by bringing the resin in question into contact with a chromium-plated steel plate.

The resin preferably has an elastic modulus at 25° C. of 1.5 GPa or lower. With the elastic modulus within the above range, the resin can constitute a housing that is soft and less likely to damage the inside of the livestock body (e.g., stomach lining). Thus, the resulting livestock sensor enables highly reliable data acquisition without giving stress to livestock.

The elastic modulus is more preferably 0.7 GPa or lower, more preferably 0.5 GPa or lower. The elastic modulus may be 0.1 GPa or higher.

The resin preferably has a mass change of lower than 0.5% during one-week immersion in a 50% by mass formic acid aqueous solution at 50° C. With the mass change within the above range, the resin can constitute a housing that is less likely to corrode even when it is in contact with an acidic body fluid such as gastric juice for a long period of time.

The mass change is more preferably 0.4% or lower, still more preferably 0.3% or lower. The mass change may be 0.1% or higher.

Examples of the resin include a fluororesin, a fluorine-free resin blended with a fluorine-containing repellent, a fluorine-free resin blended with a fluororesin, a fluoropolyether group-containing silyl compound, and a silicone resin.

Preferred among these is a fluororesin because its coefficient of kinetic friction, coefficient of static friction, and elastic modulus can be easily adjusted within the above ranges and it has excellent corrosion resistance to acids such as gastric juice.

The fluororesin preferably has a melting point of 100° C. to 360° C., more preferably 140° C. to 350° C., still more preferably 160° C. to 320° C.

The melting point is the temperature corresponding to the maximum value on a heat-of-fusion curve obtained by increasing the temperature at a rate of 10° C./min using a differential scanning calorimeter (DSC).

Examples of the fluororesin include polytetrafluoroethylene (PTFE), a tetrafluoroethylene (TFE)/perfluoro(alkyl vinyl ether) (PAVE) copolymer (PFA), a TFE/hexafluoropropylene (HFP) copolymer (FEP), an ethylene (Et)/TFE copolymer (ETFE), an Et/TFE/HFP copolymer (EFEP), polychlorotrifluoroethylene (PCTFE), a chlorotrifluoroethylene (CTFE)/TFE copolymer, a CTFE/TFE/PAVE copolymer, an Et/CTFE copolymer, polyvinyl fluoride (PVF), polyvinylidene fluoride (PVdF), a vinylidene fluoride (VdF)/TFE copolymer, a VdF/HFP copolymer, a VdF/TFE/HFP copolymer, a VdF/HFP/(meth)acrylic acid copolymer, a VdF/CTFE copolymer, a VdF/pentafluoropropylene copolymer, a VdF/PAVE/TFE copolymer, and a TFE/perfluoroalkyl allyl ether copolymer. The perfluoroalkyl allyl ether is a monomer represented by $CF_2$═$CFCF_2$—O—$Rf^4$ (wherein $Rf^4$ is a C1-C5 perfluoroalkyl group).

The fluororesin preferably includes at least one selected from the group consisting of PTFE, PFA, FEP, ETFE, a TFE/perfluoroalkyl allyl ether copolymer, and PCTFE, more preferably at least one selected from the group consisting of PTFE, PFA, FEP, and ETFE, still more preferably at least one selected from the group consisting of PTFE, PFA, and FEP, even more preferably at least one selected from the group consisting of PFA and FEP.

The PTFE may be a TFE homopolymer consisting only of a tetrafluoroethylene (TFE) unit, or may be a modified PTFE containing a TFE unit and a modifying monomer unit based on a modifying monomer copolymerizable with TFE.

The modifying monomer may be any monomer copolymerizable with TFE, and examples thereof include a perfluoroolefin such as hexafluoropropylene (HFP); a chlorofluoroolefin such as chlorotrifluoroethylene (CTFE); a hydrogen-containing fluoroolefin such as trifluoroethylene and vinylidene fluoride (VdF); a perfluorovinyl ether; a perfluoroalkyl allyl ether; a (perfluoroalkyl)ethylene; and ethylene. One type or two or more types of modifying monomers may be used.

The perfluorovinyl ether is not limited, and may be, for example, an unsaturated perfluoro compound represented by the following formula (1):

$CF_2$═CF—ORf (1)

wherein Rf is a perfluoroorganic group. The term "perfluoro organic group" herein means an organic group in which all hydrogen atoms bonded to any carbon atom are replaced by fluorine atoms. The perfluoro organic group may contain an ether oxygen.

Examples of the perfluorovinyl ether include a perfluoro (alkyl vinyl ether) (PAVE) represented by the formula (1) wherein Rf is a C1-C10 perfluoroalkyl group. The perfluoroalkyl group preferably has 1 to 5 carbon atoms.

Examples of the perfluoroalkyl group in the PAVE include a perfluoromethyl group, a perfluoroethyl group, a perfluoropropyl group, a perfluorobutyl group, a perfluoropentyl group, and a perfluorohexyl group. Preferred is perfluoro (propyl vinyl ether) (PPVE) wherein the perfluoroalkyl group is a perfluoropropyl group.

Examples of the perfluorovinyl ether further include: those represented by the formula (1) wherein Rf is a C4-C9 perfluoro(alkoxyalkyl) group, those represented by the formula (1) wherein Rf is represented by the following formula:

[Chem. 1]

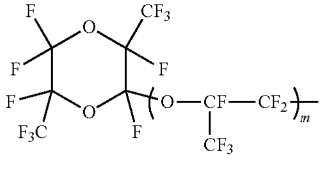

wherein m is 0 or an integer of 1 to 4; and those represented by the formula (1) wherein Rf is a group represented by the following formula:

[Chem. 2]

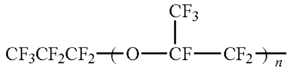

wherein n is an integer of 1 to 4.

Examples of the (perfluoroalkyl)ethylene include, but are not limited to, (perfluorobutyl)ethylene (PFBE), (perfluorohexyl)ethylene (PFHE), and (perfluorooctyl)ethylene.

The modifying monomer in the modified PTFE preferably includes at least one selected from the group consisting of HFP, CTFE, VdF, PPVE, PFBE, and ethylene, more preferably at least one selected from the group consisting of HFP and CTFE.

In the modified PTFE, the amount of the modifying monomer unit is preferably in the range of 0.00001 to 1.0% by mass. The lower limit of the amount of the modifying monomer unit is more preferably 0.0001% by mass, still more preferably 0.001% by mass, even more preferably 0.005% by mass, further preferably 0.010% by mass, particularly preferably 0.030% by mass. The upper limit of the amount of the modifying monomer unit is preferably 0.90% by mass, more preferably 0.50% by mass, still more preferably 0.40% by mass, even more preferably 0.30% by mass.

The term "modifying monomer unit" herein means a moiety that is part of the molecular structure of the modified PTFE and is derived from a modifying monomer. The term "all monomer units" herein means all moieties derived from monomers in the molecular structure of the modified PTFE.

The PTFE preferably has a melting point of 324° C. to 360° C. The melting point of PTFE means the first melting point. The first melting point is the temperature corresponding to the maximum value on a heat-of-fusion curve obtained by heating a PTFE that has no history of being heated up to a temperature of 300° C. or higher, at a rate of 10° C./min using a differential scanning calorimeter (DSC).

The PTFE preferably has a standard specific gravity (SSG) of 2.130 to 2.280. The standard specific gravity is more preferably 2.220 or lower, still more preferably 2.200 or lower, while it is preferably 2.140 or higher, more preferably 2.150 or higher. The SSG is measured by a water displacement method in conformity with ASTM D-792 using a sample molded in conformity with ASTM D 4895-89.

The PTFE preferably has non-melt secondary processibility. The non-melt secondary processibility means a property of a polymer such that the melt flow rate cannot be measured at a temperature higher than the crystallization melting point in conformity with ASTM D-1238 and D-2116.

The PFA is preferably, but is not limited to, a copolymer having a molar ratio of the TFE unit to the PAVE unit (TFE unit/PAVE unit) of 70/30 or more and less than 99/1, more preferably 70/30 or more and 98.9/1.1 or less, still more preferably 80/20 or more and 98.9/1.1 or less. The PFA is also preferably a copolymer containing 0.1 to 10 mol % (the sum of the TFE unit and the PAVE unit is 90 to 99.9 mol %), more preferably 0.1 to 5 mol %, particularly preferably 0.2 to 4 mol % of a monomer unit derived from a monomer copolymerizable with TFE and PAVE.

Examples of the monomer copolymerizable with TFE and PAVE include HFP, a vinyl monomer represented by the formula (I): $CZ^1Z^2$═$CZ^3(CF_2)_nZ^4$ (wherein $Z^1$, $Z^2$, and $Z^3$ are the same as or different from each other and each are a hydrogen atom or a fluorine atom; $Z^4$ is a hydrogen atom, a fluorine atom, or a chlorine atom; and n is an integer of 2 to 10), an alkyl perfluorovinyl ether derivative represented by the formula (II): $CF_2$=CF—$OCH_2$—$Rf^1$ (wherein $Rf^1$ is a C1-C5 perfluoroalkyl group), and an allyl ether monomer represented by the formula (X): $CZ^5Z^6$=$CZ^7$—$CZ^8Z^9$—O—$Rf^4$ (wherein $Z^5$, $Z^6$, and $Z^7$ are the same as or different from each other and each represent a hydrogen atom, a chlorine atom, or a fluorine atom; $Z^8$ and $Z^9$ each are a hydrogen atom or a fluorine atom; and $Rf^4$ is a C1-C5 perfluoroalkyl group). Examples of the allyl ether monomer include $CH_2$=$CFCF_2$—O—$Rf^4$, $CF^2$=$CFCF^2$—O—$Rf^4$ (perfluoroalkyl allyl ether), $CF_2$=$CFCH_2$—O—$Rf^4$, and $CH_2$=$CHCF_2$—O—$Rf^4$ (in the formulas, $Rf^4$ is the same as that in the formula (X)).

Examples of the monomer copolymerizable with TFE and PAVE further include unsaturated monocarboxylic acids, unsaturated dicarboxylic acids, and acid anhydrides of unsaturated dicarboxylic acids, such as itaconic acid, itaconic anhydride, citraconic anhydride, and 5-norbornene-2,3-dicarboxylic anhydride.

The PFA preferably has a melting point of 180° C. or higher and lower than 324° C., more preferably 230° C. to 320° C., still more preferably 280° C. to 320° C.

The FEP is preferably, but is not limited to, a copolymer having a molar ratio of the TFE unit to the HFP unit (TFE unit/HFP unit) of 70/30 or more and less than 99/1, more preferably 70/30 or more and 98.9/1.1 or less, still more preferably 80/20 or more and 98.9/1.1 or less. The FEP is also preferably a copolymer containing 0.1 to 10 mol % (the sum of the TFE unit and the HFP unit is 90 to 99.9 mol %), more preferably 0.1 to 5 mol %, particularly preferably 0.2 to 4 mol % of a monomer unit derived from a monomer copolymerizable with TFE and HFP.

Examples of the monomer copolymerizable with TFE and HFP include PAVE, a monomer represented by the formula (X), and an alkyl perfluorovinyl ether derivative represented by the formula (II).

Examples of the monomer copolymerizable with TFE and HFP further include unsaturated monocarboxylic acids, unsaturated dicarboxylic acids, acid anhydrides of unsaturated dicarboxylic acids, such as itaconic acid, itaconic anhydride, citraconic anhydride, and 5-norbornene-2,3-dicarboxylic anhydride.

The FEP preferably has a melting point of 150° C. or higher and lower than 324° C., more preferably 200° C. to 320° C., still more preferably 240° C. to 320° C.

The ETFE is a copolymer having a molar ratio of the TFE unit to the ethylene unit (TFE unit/ethylene unit) of preferably 20/80 or more and 90/10 or less, more preferably 37/63 or more and 85/15 or less, still more preferably 38/62 or more and 80/20 or less. The ETFE may be a copolymer of TFE, ethylene, and a monomer copolymerizable with TFE and ethylene. Examples of this copolymerizable monom include monomers represented by the following formulas: $CH_2$=$CX^1Rf^2$, $CF_2$=$CFRf^2$, $CF_2$=$CFORf^2$, and $CH_2$=C$(Rf^2)_2$ (wherein $X^1$ is a hydrogen atom or a fluorine atom, $Rf^2$ is a fluoroalkyl group optionally containing an ether bond), and a monomer represented by the formula (X). Preferred among these are fluorine-containing vinyl monomers represented by $CF_2$=$CFRf^2$, $CF_2$=$CFORf^2$, and $CH_2$=$CX^1Rf^2$ and a monomer represented by the formula (X). More preferred are HFP, a perfluoro(alkyl vinyl ether) represented by $CF_2$=CF—$ORf^3$ (wherein $Rf^3$ is a C1-C5 perfluoroalkyl group), a perfluoro(alkyl allyl ether) represented by $CF_2$=CF—$CF_2$—O—$Rf^4$ (wherein $Rf^4$ is a C1-C5 perfluoroalkyl group), and a fluorine-containing vinyl monomer represented by $CH_2$=$CX^1Rf^2$ wherein $Rf^2$ is a C1-C8 fluoroalkyl group. Examples of the monomer copolymerizable with TFE and ethylene further include unsaturated aliphatic carboxylic acids such as itaconic acid and itaconic anhydride. The monomer copolymerizable with TFE and ethylene is contained in an amount of preferably 0.1 to 10 mol %, more preferably 0.1 to 5 mol %, particularly preferably 0.2 to 4 mol % relative to the fluorine-containing polymer.

The ETFE preferably has a melting point of 140° C. or higher and lower than 324° C., more preferably 160° C. to 320° C., still more preferably 195° C. to 320° C.

The amounts of the respective monomer units in the polymer described above can be calculated by appropriate combination of NMR, FT-IR, elemental analysis, and X-ray fluorescence analysis in accordance with the types of the monomers.

The fluororesin is also preferably a melt-fabricable fluororesin. Use of a melt-fabricable fluororesin improves processibility.

The term "melt-fabricable" herein means that the polymer can be melted and processed using a conventional processor such as an extruder or an injection molding machine.

The melt-fabricable fluororesin preferably has a melt flow rate (MFR) of 0.1 to 100 g/10 min, more preferably 0.5 to 50 g/10 min.

The MFR herein is a value obtained in conformity with ASTM D1238 using a melt indexer, as the mass (g/10 min) of a polymer flowing out of a nozzle (inner diameter: 2 mm, length: 8 mm) per 10 minutes at a measurement temperature specified according to the type of the fluoropolymer (e.g., 372° C. for PFA and FEP, 297° C. for ETFE) and a load specified according to the type of the fluoropolymer (e.g., 5 kg for PFA, FEP, and ETFE).

Examples of the melt-fabricable fluororesin include those mentioned above, including PFA, FEP, ETFE, EFEP, PCTFE, and PVdF. The melt-fabricable fluororesin preferably includes at least one selected from the group consisting of PFA, FEP, and ETFE, more preferably at least one selected from the group consisting of PFA and FEP.

The housing of the disclosure preferably includes a resin layer containing the resin. The resin content of the resin layer is preferably 90% by mass or more, more preferably 95% by mass or more, still more preferably 98% by mass or more, and may be 100% by mass or less.

The housing of the disclosure may consist only of the resin layer or may be a laminate including the resin layer and a different layer. The different layer is preferably a metal layer because it has a high specific gravity. The metal contained in the metal layer is preferably stainless steel, steel, brass, copper, or the like, more preferably stainless steel.

The housing including the metal layer preferably includes a portion not including the metal layer with an aim of not completely blocking radio waves.

The laminate including the different layer preferably includes the resin layer as an outer layer, more preferably as the outermost layer.

The housing of the disclosure is preferably a member capable of containing a detector and other necessary components inside. Also, the housing of the disclosure may be configured such that a portion thereof can be separated (for example, the main body and the cap).

The housing of the disclosure may have any shape that can contain a detector and other necessary components inside, such as a tubular shape (e.g., circular tube, square tube), a bottle shape, a bottomed circular tubular shape, and a bottomed square tubular shape. Preferred among these are a tubular shape, a bottle shape, a bottomed circular tubular shape, and a bottomed square tubular shape, and more preferred are a circular tubular shape and a bottomed circular tubular shape.

The housing of the disclosure can be produced by molding the resin by a known molding method such as cutting, injection molding, extrusion molding, or compression molding.

In the case of providing the above-described different layer, a known lamination method may be employed. One preferred method includes covering the outer peripheral surface of a tubular base material (different layer) with a tube made of the resin and heat-shrinking the tube. Alternatively, a coating material containing the resin may be applied to the different layer.

The housing of the disclosure is for a livestock sensor and is used to configure a livestock sensor.

The present disclosure also relates to a livestock sensor including the housing for a livestock sensor of the disclosure described above and a detector inside the housing.

The livestock sensor of the disclosure including the housing of the disclosure is slippery, which facilitates swallowing of the sensor by livestock, allowing for easy oral administration. Such a livestock sensor enables highly reliable data acquisition without giving stress to livestock. Use of the housing of the disclosure also reduces the limitation on the shape or size of the housing and therefore can increase the design flexibility.

The livestock sensor is placed in the livestock body and detects the state of the livestock (e.g., pH, temperature, amount of exercise (acceleration)). The livestock sensor is preferably configured to be orally administered to livestock. Further, the livestock sensor is preferably a wireless transmission sensor capable of wirelessly transmitting acquired data.

Examples of the detector include a pH sensor, a temperature sensor, a piezoelectric sensor, an acceleration sensor, and a position sensor.

The livestock are preferably ruminant animals including cattle (dairy cattle, beef cattle), sheep, and goats. Cattle are particularly preferred.

The livestock sensor is preferably placed in an internal organ of livestock, more preferably in the stomach, still more preferably in the rumen, particularly preferably in the rumen fluid.

The livestock sensor is preferably left in the livestock body for one month or longer, more preferably six months or longer, still more preferably one year or longer, particularly preferably three years or longer.

The livestock sensor preferably has a specific gravity of 1.8 or higher, more preferably 2.0 or higher. The livestock sensor having a specific gravity within the above range can be easily placed (submerged) in a body fluid such as gastric juice.

The livestock sensor may have any size that allows oral administration to livestock. In the case of the circular tubular sensor, the diameter may be 10 to 35 mm and the length may be 40 to 150 mm, for example.

The FIGURE shows an exemplary structure of the livestock sensor of the disclosure. The livestock sensor of the disclosure is not limited to this.

A livestock sensor 10 in the FIGURE includes a housing 11. The housing 11 corresponds to the housing of the disclosure.

The housing 11 contains a signal processing circuit 13 connected to a battery 12. The signal processing circuit 13 is provided with an acceleration sensor 14 and a radio transmitter 17. To the signal processing circuit 13 are electrically connected a temperature sensor 15 and a fixed pH sensor 16.

The temperature sensor 15 and the fixed pH sensor 16 are partly exposed outside the housing 11 so as to contact with the rumen fluid.

The disclosure relates to a housing for a livestock sensor, the housing including: a resin having a coefficient of kinetic friction of 0.40 or lower and a coefficient of static friction of 0.10 or lower.

The resin preferably has an elastic modulus at 25° C. of 1.5 GPa or lower.

The resin is preferably a fluororesin.

The resin preferably includes at least one selected from the group consisting of polytetrafluoroethylene, a tetrafluoroethylene/perfluoro(alkyl vinyl ether) copolymer, a tetrafluoroethylene/hexafluoropropylene copolymer, an ethylene/tetrafluoroethylene copolymer, a tetrafluoroethylene/perfluoroalkyl allyl ether copolymer, and polychlorotrifluoroethylene.

The resin is preferably a melt-fabricable fluororesin.

The resin preferably has a mass change of lower than 0.5% during one-week immersion in a 50% by mass formic acid aqueous solution at 50° C.

The disclosure also relates to a livestock sensor including: the housing; and a detector inside the housing.

EXAMPLES

The disclosure will be described in more detail with reference to examples, but the disclosure is not limited only to these examples.

The resins used in the test example, examples, and comparative examples are shown below.

PTFE: TFE homopolymer (melting point: 327° C., SSG: 2.2)

PFA: TFE/PPVE copolymer (melting point: 306° C., MFR: 1 g/10 min)

FEP: TFE/HFP copolymer (melting point: 265° C., MFR: 2 g/10 min)

ETFE: Et/TFE copolymer (melting point: 265° C., MFR: 5 g/10 min)

PCTFE: CTFE homopolymer (melting point: 210° C., flow value: $1.5\times10^{-3}$ cc/s (230° C., 980 N, nozzle diameter 1 mm))

High-density polyethylene (HDPE): Novatec HD HJ490 available from Japan Polyethylene Corporation Low-density polyethylene (LDPE): J2522 available from Ube-Maruzen Polyethylene Co., Ltd.

Polypropylene (PP): Novatec PP BC2E available from Japan Polyethylene Corporation Polystyrene (PS): GPPS 679 available from PS Japan Corporation Polyvinyl chloride (PVC): Kanevinyl S-400 available from Kaneka Corporation Nylon: UBE NYLON 1024JI available from Ube Industries, Ltd.

Polycarbonate (PC): Iupilon H-3000 available from Mitsubishi Engineering-Plastics Corporation The MFR values are measured in conformity with ASTM D1238. The flow value of PCTFE is measured using a Koka flow tester.

Test Example 1

Sheets each having a thickness of 0.2 mm and a diameter of 120 mm were produced from the respective resins by compression molding using a heat press. PTFE was molded at a temperature that is 50° C. to 70° C. higher than the melting point and at a pressure of 5 MPa. Other resins were each molded at a temperature that is 40° C. higher than the melting point and at a pressure of 3 MPa.

Using the resulting sheets, the coefficient of kinetic friction, the coefficient of static friction, and the elastic modulus were measured by the following methods. Table 1 shows the results.

<Coefficient of Kinetic Friction, Coefficient of Static Friction>

The sheets were each brought into contact with a chromium-plated steel plate at room temperature in conformity with JIS K 7125 for the measurements.

<Elastic Modulus>

The elastic modulus was measured at 25° C. in conformity with ASTM D638.

TABLE 1

| Resin | PTFE | PFA | FEP | PCTFE | ETFE | HDPE | LDPE | PP | PS | PVC | Nylon | PC |
|---|---|---|---|---|---|---|---|---|---|---|---|---|
| Coefficient of kinetic friction | 0.03 | 0.04 | 0.08 | 0.10 | 0.40 | 0.13 | 0.13 | 0.37 | 0.47 | 0.25 | 0.08 | 0.45 |
| Coefficient of static friction | 0.02 | 0.05 | 0.05 | 0.08 | 0.06 | 0.36 | 0.36 | 0.40 | 0.47 | 0.41 | 0.71 | 0.53 |
| Elastic modulus (Mpa) | 390 | 440 | 340 | 1500 | 640 | 690 | 170 | 1300 | 3000 | 2900 | 1800 | 2500 |

Examples 1 to 5 and Comparative Examples 1 and 2

A SUS304 housing with a diameter of 30 mm and a length of 150 mm was covered with a heat-shrink tube that was made of the resin shown in Table 2 and had a diameter of 36 mm, a wall thickness of 0.5 mm, and a length of 170 mm. The tube was shrunk by heating for 10 minutes at a temperature 20° C. higher than the melting point of the heat-shrink tube, whereby the SUS housing was covered with the resin. A Sensor was installed in each housing covered with the resin, and the resulting products (samples) were subjected to the following simulated swallowing test. Table 2 shows the results.

<Simulated Swallowing Test>

The time required for the sample to pass through a neoprene rubber tube (diameter: 40 mm, length: 1000 mm) set at an angle of 45 degrees was measured and evaluated based on the following criteria.

Good: Shorter than 10 seconds

Acceptable: Shorter than 20 seconds

Poor: 20 Seconds or longer or sample did not come out

<Chemical Resistance>

A sample (the sheet or stainless steel) was immersed in a 50% by mass formic acid aqueous solution at 50° C. for one week. The mass change during the immersion was determined and evaluated based on the following criteria. If the sample had cracks, rust, or like deterioration, it was rated as Poor regardless of the mass change.

Good: Mass change of lower than 0.5%

Acceptable: Mass change of 0.5% or higher and lower than 10%

Poor: Mass change of 10% or higher

TABLE 2

| | | Example 1 | Example 2 | Example 3 | Example 4 | Example 5 | Comparative Example 1 | Comparative Example 2 |
|---|---|---|---|---|---|---|---|---|
| Material | Base material | SUS | SUS | SUS | SUS | SUS | SUS | SUS |
| | Surface | PFA | FEP | PCTFE | ETFE | PTFE | PS | — |
| Evaluation | Simulated swallowing test | Good | Good | Good | Good | Good | Poor | Poor |
| | Chemical resistance | Good | Good | Good | Good | Good | Good | Poor |

REFERENCE SIGNS LIST

10: livestock sensor
11: housing
12: battery
13: signal processing circuit
14: acceleration sensor
15: temperature sensor
16: fixed pH sensor
17: radio transmitter

What is claimed is:

1. A housing for a livestock sensor, the housing comprising:

a resin having a coefficient of kinetic friction of 0.40 or lower and a coefficient of static friction of 0.10 or lower, and the resin being other than polytetrafluoroethylene, wherein the coefficient of kinetic friction and the coefficient of static friction are measured by bringing the resin into contact with a chromium-plated steel plate at room temperature in conformity with JIS K 7125.

2. The housing for a livestock sensor according to claim 1, wherein the resin has an elastic modulus at 25° C. of 1.5 GPa or lower.

3. The housing for a livestock sensor according to claim 1, wherein the resin is a fluororesin.

4. The housing for a livestock sensor according to claim 1, wherein the resin includes at least one selected from the group consisting of a tetrafluoroethylene/perfluoro(alkyl vinyl ether) copolymer, a tetrafluoroethylene/hexafluoropropylene copolymer, an ethylene/tetrafluoroethylene copolymer, a tetrafluoroethylene/perfluoroalkyl allyl ether copolymer, and polychlorotrifluoroethylene.

5. The housing for a livestock sensor according to claim 1, wherein the resin is a melt-fabricable fluororesin.

6. The housing for a livestock sensor according to claim 1, wherein the resin has a mass change of lower than 0.5% during one-week immersion in a 50% by mass formic acid aqueous solution at 50° C.

7. The housing for a livestock sensor according to claim 1, wherein the resin has an elastic modulus at 25° C. of 440 MPa or higher.

8. A livestock sensor comprising:

the housing for a livestock sensor according to claim 1; and a detector inside the housing.

* * * * *